United States Patent [19]
Rizzo et al.

[11] Patent Number: 5,882,900
[45] Date of Patent: Mar. 16, 1999

[54] PROCESS FOR THE SELECTIVE INCREASE OF PRODUCTION OF ANTIBIOTIC GE 2270 FACTOR A BY ADDING VITAMIN B12 TO NUTRIENT MEDIUM

[75] Inventors: Angelo Michele Rizzo, Mesagne; Luciano Gastaldo, Pogliano Milanese, both of Italy

[73] Assignee: Gruppo Lepetit S.p.A., Italy

[21] Appl. No.: 940,697

[22] Filed: Sep. 30, 1997

Related U.S. Application Data

[63] Continuation of Ser. No. 746,136, Nov. 6, 1996, abandoned, which is a continuation of Ser. No. 574,910, Mar. 1, 1995, abandoned, which is a continuation-in-part of PCT/EP93/01907 Jul. 20, 1993.

[30] Foreign Application Priority Data

Sep. 10, 1992 [EP] European Pat. Off. .............. 92115451

[51] Int. Cl.$^6$ ............................ C12P 21/04; A61K 38/00
[52] U.S. Cl. ....................... 435/71.3; 435/71.1; 435/71.2; 435/822; 514/9
[58] Field of Search ................... 435/71.1, 71.2, 435/71.3, 822; 514/9

[56] References Cited

U.S. PATENT DOCUMENTS

| | | | |
|---|---|---|---|
| 4,032,404 | 6/1977 | Tomita et al. ............................. | 435/80 |
| 5,139,778 | 8/1992 | Selva et al. ............................. | 424/117 |
| 5,202,241 | 4/1993 | Selva et al. ............................. | 435/71.3 |
| 5,322,777 | 6/1994 | Selva et al. ............................. | 435/71.3 |
| 5,514,649 | 5/1996 | Selva et al. ................................ | 514/9 |
| 5,599,791 | 2/1997 | Tavecchia et al. ........................... | 514/9 |

FOREIGN PATENT DOCUMENTS

| | | |
|---|---|---|
| 451 486 | 10/1991 | European Pat. Off. . |
| 0048999 | 7/1992 | European Pat. Off. . |
| WO 97/30078 | 8/1997 | WIPO . |

OTHER PUBLICATIONS

The Merck Index, 11$^{th}$ Edition, p. 1577.
Krasnova, TP, et al., Antibiotiki 23, No. 1, 12–18, 1978.
Laznikova TN, et. al, Antibiotiki 23 No. 6, 499–503, 1978.
Laznikova TN, et. al., Antibiotiki 22, No. 2, 102–108, 1977.
Krasnova TP, et al., Antibiotiki 24, No. 5, 323–328, 1979.
Krasnova TP, et al., Antibiotiki 22, No.3, 201–206, 1977.
Krasnova TP, et al., Antibiotiki 24, No. 11, 808–815, 1979.
Tavecchia P., et al., J. Antibiotics (Tokyo) 1994, 47, 1564–1567.
Stryer, L. Biochemistry, 3$^{rd}$ Ed. W.H. Freeman & Co., 1988, p. 507.
Bogert et al. Nutrition and Physical Fitness, 9$^{th}$ Ed. W.B. Saunders Co. pp. 569–574.
Selva et al. J. Antibiot. vol. 44, pp. 693–701 (1991).

*Primary Examiner*—Leon B. Lankford, Jr.
*Assistant Examiner*—Christopher R. Tate
*Attorney, Agent, or Firm*—Killworth, Gottman, Hagan & Schaeff, L.L.P.

[57] ABSTRACT

A method for increasing both total antibiotic yield the selective production of factor A of the GE 2270 antibiotics consisting in the addition of vitamin $B_{12}$ or its analogs having vitamin $B_{12}$—like activity to the fermentation media of *Planobispora rosea* ATCC 53773 or any antibiotic GE 2270 producing mutant or variant thereof.

12 Claims, No Drawings

PROCESS FOR THE SELECTIVE INCREASE OF PRODUCTION OF ANTIBIOTIC GE 2270 FACTOR A BY ADDING VITAMIN B12 TO NUTRIENT MEDIUM

This is a continuation of application Ser. No. 08/746,136, filed Nov. 6, 1996 now abandoned, which is a continuation of application Ser. No. 08/574,910, filed Mar. 1, 1995, now abandoned, which is herein incorporated by reference.

This is a continuation-in-part of International Patent Application No. PCT/EP93/01907 designating the United States of America and having the International filing date of Jul. 20, 1993.

Antibiotic GE 2270 is a thiazolyl peptide substance isolated from a culture of *Planobispora rosea* ATCC 53773 (deposited Jun. 6, 1988 with the American Type Culture Collection, 12301 Parklawn Drive, Rockville, Md. 20852).

This substance, which is mainly active against gram positive bacteria as well as some gram negative anaerobes, is described in European Patent Application Publication No. 359062 (as well as U.S. Pat. No. 5,202,241, issuing Apr. 13, 1993, which is hereby incorporated by reference) together with the process for obtaining it and the corresponding pharmaceutical compositions.

Antibiotic GE 2270 is produced by the microorganism as a complex of the closely related components A, B1, B2, C1, C2, C2a, D1, D2, E, and T which have been isolated and characterized.

Factor A, which is the component obtained in preponderant amount and the most relevant for the biological activity, is described in the above mentioned European Patent Application Publication N. 359062 together with the process for its isolation and its uses (see also: E. Selva et al., "Antibiotic GE 2270 A: A Novel Inhibitor of Bacterial Protein Synthesis. I.Isolation and Characterization". The Journal of Antibiotics, Vol. 44 No. 7, 693–701, 1991; J. Kettenring et al, "Antibiotic GE 2270 A: A Novel Inhibitor of Bacterial Protein Synthesis. II. Structure Elucidation". The Journal of Antibiotics, Vol.44 No.7, 702–715, 1991).

Factor A is utilized as starting material for the preparation of antibiotic GE 2270 factors A1, A2, A3, (by hydrolysis) and H (by treatment with a reducing agent, e.g. $NaBH_4$).

Factors B1, B2, C1, C2, D1, D2, E, and T as well as the process for their isolation and uses are described in European Patent Application Publication No. 451486 (and in U.S. patent application Ser. No. 08/144,102 filed on Oct. 27, 1993 and which is hereby incorporated by reference). Factor C2a and its process of isolation is described in European Patent Application Publication No. 529410 (corresponding to U.S. patent application Ser. No. 07/931084 filed on Aug. 17, 1992, which is hereby incorporated by reference).

The preparation of Antibiotic GE 2270 factors A1, A2, A3, and H from GE 2270 factor A is described in European Patent Application Publication No. 406745(and in U.S. Pat. No. 5,355,333 which was filed on Oct. 13, 1993 and is hereby incorporated by reference). See also E. Selva et al., "Natural Antibiotics Related to GE 2270 A.: Isolation, Structure Elucidation and Biological Characterization", 31st ICAAC, Sep. 29–Oct. 2, 1991, Chicago. In said paper factor C2 is identified as C2b.

The structures of the components of the complex GE 2270 are set forth in Table I.

TABLE I

Structure of GE 2270 factors

| GE 2270 Factor | $R_1$ | $R_2$ | $R_3$ | $R_4$–$R_5$ |
|---|---|---|---|---|
| A | $CH_3$ | $CH_3$ | $CH_2OCH_3$ | $CH_2$–CH |
| B1 | $CH_3$ | H | $CH_2OCH_3$ | $CH_2$–CH |
| B2 | $CH_3$ | $CH_3$ | $CH_3$ | $CH_2$–CH |
| C1 | $CH_3$ | $CH_3$ | H | $CH_2$–CH |
| C2 | H | $CH_3$ | $CH_2OCH_3$ | $CH_2$–CH |
| C2a | $CH_2OH$ | $CH_3$ | $CH_2OCH_3$ | $CH_3$–CH |
| D1 | $CH_3$ | H | H | $CH_2$–CH |
| D2 | $CH_3$ | $CH_3$ | $CH_2OH$ | $CH_2$–CH |
| E | $CH_3$ | H | $CH_2OH$ | $CH_2$–CH |
| T | $CH_3$ | $CH_3$ | $CH_2OCH_3$ | CH=C |

Due to the increasing development of tolerance and even resistance to current antibiotic treatments, the need for new antibiotic substances is still high. Particularly desirable are antibiotics in single isolated form with well defined and standardized composition assuming constant physico-chemical (e.g. stability) and biological (e.g. pharmacokinetics) behavior.

The current fermentation method described in EP-A 359062 yield a complex mixture wherein the factor A is generally less than 70% (by HPLC) with a total antibiotic productivity generally lower than 300 ppm. According to this invention it has been found that addition of vitamin $B_{12}$ (cyanocobalamin) or its analog having vitamin $B_{12}$—like activity wherein the cyano group is replaced by another ligand, to the fermentation medium employed for production of the GE 2270 antibiotic complex enhances both the total antibiotic complex yield and the selectivity in the production of factor A.

Examples of analogs of vitamin $B_{12}$ having vitamin $B_{12}$—like activity are, for instance, hydroxocobalamin, 5'-deoxyadenosyl-cobalamin, methylcobalamin as well as those listed in the book "THE VITAMINS", Chemistry, Physiology, Pathology, Methods" edited by W. H. Sebrell and R. S. Harris, Vol. II, pag. 181, Academic Press, New York—London, 1968.

Antibiotic production improvements due to the effect of vitamin $B_{12}$ are reported in literature for monensins, fortimicin, gentamycin, chuangxinmycin, SF-2312, antibiotic having heptemic acid skeleton (thienamycin, PS-5, etc.), elsamicin and leinamycin.

However, it does not appear that a simultaneous double effect showing an increase of total antibiotic yield and a highly selective production of one of the components of the complex has been observed.

Detailed studies have been done on gentamycin producing strains of *Micromonospora purpurea*, by Russian authors (T. P. Krasnova et al.; "Comparative Studies on Active Strain of *Micromonospora purpurea* and its Low Active Mutant in Connection with Biosynthesis of Gentamycin". Antibiotics 24, No. 5, 323–328, 1979; Ringdog Abstract 31044U). Their results could be summarized as follows:

(a) Additions of cobalt to the fermentation medium stimulates the biosynthesis of vitamin $B_{12}$ and influences the antibiotic complex composition.

(b) The mechanism proposed for the effect of the cobalt addition is that the cobalt ion stimulates the synthesis of the endogeneus vitamin $B_{12}$ necessary for the synthesis of methionine which is a source of methyl groups.

In experiments made by the inventors with GE 2270, only a moderate effect of $COCl_2$ addition has been noted while the factor A selectivity was slightly influenced and the overall GE 2270 synthesis was slightly increased to values of the order of 300 ppm.

The amounts of vitamin $B_{12}$ or its analogs to be added to the fermentation medium in order to reach the desired effect according to this invention usually vary depending on the producing strain and composition of the culture medium utilized. Simple laboratory scale tests allow the person skilled in the art to determine the appropriate amounts of vitamin $B_{12}$ or its analogs to be added to the fermentation medium.

Under the usual fermentation conditions the effective amount generally ranges between 0.0005 and 5 ppm. Amounts larger than 5 ppm may be employed but without any substantial enhancement of the effect which can be reached with the upper value of the above interval. A preferred addition of vitamin $B_{12}$ ranges between 0.005 and 1 ppm.

The vitamin $B_{12}$ can be added as a free compound (e.g. crystalline vitamin $B_{12}$), as a concentrate or as a component of a more complex material which can be added to the fermentation medium. Said material should be acceptable for the fermentation conditions required for the production of the antibiotic GE 2270, i.e., it should not be toxic to the mentioned strain and should not negatively effect its growth and productivity.

Preferably, this material can be utilized by the microorganism also as an effective source of the essential elements for its growth, that is, it can be utilized also as source of carbon, nitrogen and/or mineral salts. For instance, vitamin $B_{12}$ activity is contained in both standard and de-fatted fish meal. Addition of an appropriate amount of fish meal to the fermentation medium can therefore act as an assimilable nitrogen source and simultaneously provide the necessary amount of vitamin $B_{12}$ to obtain the effect of this invention.

The fermentation media and the culturing process conditions utilized in the method of this invention are essentially those already described in the above mentioned EP-A 359062. *Planobispora rosea* ATCC 50773 or any antibiotic GE 2270 producing mutant or variant thereof is employed as antibiotic GE 2270 producing microorganism. Said variants or mutants may be obtained for instance by treatment with various known mutagens as indicated in the above mentioned EP-A 359062.

In summary, this invention consists in a fermentation process for the production of antibiotic GE 2270 complex in high yield and selectively enriched in the predominant factor A by cultivation of the strain *Planobispora rosea* ATCC 50773 or any antibiotic GE 2270 producing mutant or variant thereof under submerged aerobic conditions in the presence of assimilable sources of carbon, nitrogen and inorganic salts characterized in that vitamin $B_{12}$, or its analogs having vitamin $B_{12}$—like activity wherein the cyano group is replaced by another ligand, is added to the fermentation medium.

As explained above, the fermentation procedures utilized according to this invention are essentially the same as those described in the state of the art for producing antibiotic GE 2270 complex. Frozen culture samples of *Planobispora rosea* are used to inoculate a flask or a vessel containing vegetative medium. The cultures are then incubated with shaking at a temperature between 26° C. and 37° C. for a sufficient time to achieve a desired growth. At a temperature between 28° C. and 30° C. an incubation time of 60–75 hours is generally sufficient for a satisfactory growth. After this period, aliquots of the obtained cultures are transferred into flasks or vessels containing the fermentation medium additioned with the appropriate amounts of vitamin $B_{12}$ or its analogs. If the vitamin $B_{12}$ is added as a component of a complex material or, preferably, as a component of a nutrient material of the fermentation medium, said material should be dosed in relation to its content of vitamin $B_{12}$. The dosage required to obtain the effect of this invention may be determined by carrying out a series of cultivation experiments wherein different concentrations of the selected material are added to the fermentation medium or by predetermining the contents of vitamin $B_{12}$ of the said material by solvent (i.e. benzyl alcohol, phenol or butanol) extraction and chromatographic separation/analysis of the extract.

However, in some cases, there is a limitation of the amount of material that can be added to the fermentation broth since above certain concentration values some materials show a general depressing effect on the microorganism producing the GE 2270 complex.

For instance, it has been observed that a certain type of fish meal (Agras type 99.9 herring fish meal produced by: FISKERINDUSTRY AMBA, Kiskeri Havnsgade 35,6701 Esbjer, Denmark), which at dosages between 1 and 15 g/liter promotes both the increase of total GE 2270 complex productivity and the increase of selective production of factor A, at concentration of 20 g/liter practically inhibits the growth of the microorganism and the production of the antibiotic. Such effect was not observed with the addition of de-fatted fish meal Agras type 99.9.

The flask or vessels containing the standard fermentation medium and the appropriate amount of vitamin $B_{12}$, after inoculation with the above mentioned culture, are kept at a temperature between 24° C. and 37° C., preferably, between 28° C. and 30° C., with shaking or stirring for a period sufficiently long for achieving the maximum yield of antibiotic GE 2270 complex. This period is essentially determined by monitoring the fermentation course by analytical procedures, including bioassays, such as paper disc or agar diffusion assays on sensible microorganisms (e.g. *Bacillus subtilis* or *S. aureus*), TLC or HPLC procedures commonly utilized in the art (see EP-A 359062).

In general a fermentation period sufficient for achieving the maximum yield of antibiotic GE 2270 under the conditions utilized according to this invention ranges from 3 to 7 days.

The composition of the standard pre-culture and the fermentation media utilized for carrying out the method of this invention contain the nutrient materials usually employed in the art. Certain nutrient materials are however preferred.

Preferred carbon sources are glucose, mannose, galactose, starch, corn meal and the like. Preferred nitrogen sources are ammonia, nitrates, soybean meal, peptone, hydrolyzed casein, meat extract, yeast extract, tryptone, aminoacids, and the like. Among the inorganic salts which can be incorporated in the culture media there are the customary soluble salts capable of yielding sodium, potassium, iron, zinc, cobalt, magnesium, calcium, ammonium, chloride, carbonate, sulfate, phosphate, nitrate and the like ions.

For example, a standard fermentation medium (without considering the addition of vitamin $B_{12}$ or its analogs) may contain soluble starch, hydrolyzed casein, yeast extract meat extract, soyben meal, glucose and calcium carbonate. To the nutrient components described above, other materials can be added in case the vitamin $B_{12}$ is supplemented as a component of a complex material. Fish meal, animal organ extracts, raw extracts from vitamin $B_{12}$ microbial productions are representative examples of said complex material containing vitamin $B_{12}$.

A particular effect on both the selectivity in factor A production and the total potency of the fermentation broth has been observed when ammonium sulfate is added to the fermentation medium. The preferred concentrations of ammonium sulfate range between 0.5 and 1.5 g/l.

When the fermentation is stopped, the antibiotic GE 2270 complex which is obtained under the general conditions of this invention usually contains more than 80% (HPLC) of factor A. By carrying out the fermentation process under the most preferred conditions final concentrations of total antibiotic GE 2270 complex of the order of 350–500 ppm in the fermentation broth can be obtained, with a ratio of factor A of about 95% (HPLC).

The antibiotic product can be recovered from the fermentation broth and purified according to the methods previously disclosed. (See EP-A 359062). In particular, with the crude GE 2270 contains the factor A in a proportion over 90%, it can be directly purified by crystallization from an organic solvent or a mixture of organic solvents yielding a product which contains less than 5% of the total other factors.

The following examples describes some representative ways to carry out the method of this invention.

EXAMPLE 1

Fermentation Procedures 1.1) Microorganism: The microorganism used is *Planobispora rosea* ATCC 53773 or a GE 2270 producing mutant or variant thereof which is stored in frozen culture broths maintained at −80° C. for use as working stocks.
The storage medium has the following composition:

| | |
|---|---|
| Soluble starch | 20 g/liter |
| Polypeptone | 5 g/liter |
| Yeast extract | 3 g/liter |
| Meat extract | 2 g/liter |
| Soybean meal | 2 g/liter |
| $CaCO_3$ | 1 g/liter |

1.2) Fermentation conditions: Pre-cultures are prepared in 500 ml Erlenmeyer flasks by inoculating with 5 ml of the above frozen culture the flasks containing the same medium as above.

The inoculated flasks are incubated for 72 hours at 28° C. with shaking (200 rpm), then 4 ml aliquotes of the culture broth are transferred to the flasks containing the following medium additioned with the selected amount of vitamin $B_{12}$ or its analogs.

| | |
|---|---|
| Soluble starch | 35 g/liter |
| Hydrolysed casein | 5 g/liter |
| Yeast extract | 8 g/liter |
| Meat extract | 3.5 g/liter |
| Soybean meal | 3.5 g/liter |
| Glucose | 10 g/liter |
| $CaCO_3$ | 2 g/liter |

This medium is prepared in distilled water and the pH is corrected to 7.2 before sterilization (122° C. for 30 minutes). Each medium contains 0.03% of Hodag AFM-5 as antifoaming agent.

The fermentation is carried out for 7 days at 28° C.–30° C. with shaking (200 rpm), during which period the fermented broths are monitored for the antibiotic production.

1.3) Vitamin $B_{12}$ Additions:

1.3.1) Vitamin $B_{12}$ or its analogs are dissolved in distilled water at a starting concentrations of 25 mg/ml and are diluted in water. The solution are sterilized by filtration and added to the fermentation medium described above at the selected concentration.

1.3.2) Fish meals (Agras type 99.9 and Agras type 99.9 de-fatted) are added to the fermentation flasks containing the above medium on the selected amounts.

1.4) HPLC Analysis of the Antibiotic Production:

One volume of the fermented broth is extracted with two volumes of acetonitrile by stirring at room temperature for about 20 minutes and the suspension is centrifuged for 5 minutes at 3.000 rpm. The solution obtained is used for the HPLC analysis by assuming a dilution ratio 1:3.

HPLC Conditions:

| | |
|---|---|
| Instrument: | HP 1082 with UV 254 detector |
| Column: | Brownlee RP-18 5$\mu$ 22 cm |
| Precolumn: | Brownlee RP-18 5$\mu$ 1.5 cm |
| Eluent phase A: | $NaH_2PO_4$ 20 mM - $CH_3CN$ 90:10 |
| Eluent phase B: | $NaH_2PO_4$ 20 mM - $CH_3CN$ 30:70 |
| Gradient type: | linear |
| Gradient time: | 20 min. from 45% B to 75% B |
| Flow rate: | 1.5 ml/min. |
| Injection: | 30 $\mu$l |

Under the above conditions, all peaks of the HPLC chromatographic profile falling within the retention times ($R_t$) interval from 6.20 to 13.67 minutes are related to the factors of the GE 2270 complex. Factor A shows a $R_t$ value of 11.65 minutes.

EXAMPLE 2

Effects of Addition of Vitamin $B_{12}$ or its Analogs 2.1) The following Table 1 reports two experiments showing the effects of the addition of vitamin $B_{12}$ at various concentration to the fermentation medium. Estimations are made by HPLC methods.

TABLE 1

| Vitamin $B_{12}$ p.p.m. | Total GE 2270 complex p.p.m. | Factor A p.p.m. | Factor A % |
|---|---|---|---|
| Experiment 1 | | | |
| Control (no addition) | 312 | 192 | 61.6 |
| 0.01 | 369 | 347 | 94.1 |
| 0.05 | 340 | 321 | 94.3 |
| 0.10 | 410 | 387 | 94.3 |
| 0.50 | 319 | 299 | 93.8 |
| 1.00 | 378 | 356 | 94.5 |
| 2.00 | 408 | 385 | 94.4 |
| 5.00 | 422 | 398 | 94.2 |
| 10.00 | 366 | 347 | 94.8 |
| 20.00 | 340 | 321 | 94.4 |
| Experiment 2 | | | |
| 1.00 | 336 | 311 | 92.5 |
| 0.10 | 416 | 384 | 92.3 |
| 0.01 | 426 | 393 | 92.5 |
| 0.005 | 401 | 368 | 91.5 |
| 0.001 | 318 | 265 | 83.3 |
| 0.0005 | 345 | 284 | 82.4 |
| 0.00001 | 336 | 263 | 78.2 |
| Control (no addition) | 320 | 249 | 77.8 |

2.2) The following Table 2 shows the effect of the addition of methylcobalamin at various concentrations to the fermentation medium.

TABLE 2

| Methyl-cobalamin | Factor A p.p.m. | Factor A % |
|---|---|---|
| Control (no addition) | 87 | 47.0 |
| 0.001 | 235 | 83.1 |
| 0.01 | 280 | 91.6 |
| 0.10 | 297 | 93.2 |
| 1.00 | 290 | 92.2 |

2.3) The following Table 3 shows the effects of the addition of various amounts of fish meal to the fermentation medium.

TABLE 3

| Fish meal | Factor A p.p.m. | Factor A % |
|---|---|---|
| Control (no addition) | 99 | 46.5 |
| Agras type 99.9 (g/l) | | |
| 1 | 206 | 68.8 |
| 2.5 | 282 | 82.2 |
| 5 | 310 | 88.8 |
| 7.5 | 340 | 88.4 |
| 10 | 373 | 89.6 |
| 15 | 300 | 91.6 |
| 20 | 4 | — |
| 30 | 1 | — |
| Agras type 99.9 de-fatted (g/l) | | |
| 5 | 355 | 93.9 |
| 10 | 466 | 93.9 |
| 20 | 445 | 92.8 |

We claim:

1. In a fermentation process for the production of antibiotic GE 2270 complex in high yield and selectively enriched in the predominant factor A whereby a strain of *Planobispora rosea* ATCC 53773, or a mutant or variant thereof is cultured under submerged conditions in a nutrient medium containing assimilable sources of carbon, nitrogen, and inorganic salts, the improvement comprising adding from 0.0005 to 5 ppm of vitamin $B_{12}$ to the nutrient medium, wherein the vitamin $B_{12}$ may optionally be in the form of an analog of vitamin $B_{12}$ wherein the cyano group of vitamin $B_{12}$ is replaced by another ligand or wherein the vitamin $B_{12}$ may optionally be in the form of 1 to 15 g/L of fish meal or de-fatted fish meal.

2. The process according to claim 1 further comprising the addition of 0.5 to 1.5 g/L of ammonium sulfate to the nutrient medium.

3. The process according to claim 1, wherein the vitamin $B_{12}$ or its analog are selected from vitamin $B_{12}$, hydroxocobalamin, 5'-deoxadenosylcobalamin, and methylcobalamin.

4. The process according to claim 2, wherein the vitamin $B_{12}$ or its analog are selected from vitamin $B_{12}$, hydroxocobalamin, 5'-deoxadenosylcobalamin, and methylcobalamin.

5. The process according to claim 1, wherein the amount of the vitamin $B_{12}$ or analog of vitamin $B_{12}$ is added to the nutrient medium ranges 0.005 to 1 ppm.

6. The process according to claim 2, wherein the amount of the vitamin $B_{12}$ or analog of vitamin $B_{12}$ is added to the nutrient medium ranges 0.005 to 1 ppm.

7. The process according to claim 3, wherein the amount of the vitamin $B_{12}$ or analog of vitamin $B_{12}$ is added to the nutrient medium ranges 0.005 to 1 ppm.

8. The process according to claim 4, wherein the amount of the vitamin $B_{12}$ or analog of vitamin $B_{12}$ is added to the nutrient medium ranges 0.005 to 1 ppm.

9. The process according to claim 1 wherein the fish meal or de-fatted fish meal is Agras type 99.9 herring fish meal or de-fatted Agras type 99.9 herring fish meal.

10. The process according to claim 2 wherein the fish meal or de-fatted fish meal is Agras type 99.9 herring fish meal or de-fatted Agras type 99.9 herring fish meal.

11. The process according to claim 3 wherein the fish meal or de-fatted fish meal is Agras type 99.9 herring fish meal or de-fatted Agras type 99.9 herring fish meal.

12. The process according to claim 4 wherein the fish meal or de-fatted fish meal is Agras type 99.9 herring fish meal or de-fatted Agras type 99.9 herring fish meal.

* * * * *